United States Patent
Green

(10) Patent No.: US 9,881,781 B2
(45) Date of Patent: Jan. 30, 2018

(54) OPTIMIZED MULTIPLE REACTION MONITORING OR SINGLE ION RECORDING METHOD

(71) Applicant: Micromass UK Limited, Wilmslow (GB)

(72) Inventor: Martin Raymond Green, Bowdon (GB)

(73) Assignee: MICROMASS UK LIMITED, Wilmslow (GB)

(*) Notice: Subject to any disclaimer, the term of this patent is extended or adjusted under 35 U.S.C. 154(b) by 0 days.

(21) Appl. No.: 15/116,587

(22) PCT Filed: Feb. 4, 2015

(86) PCT No.: PCT/GB2015/050300
§ 371 (c)(1),
(2) Date: Aug. 4, 2016

(87) PCT Pub. No.: WO2015/118321
PCT Pub. Date: Aug. 13, 2015

(65) Prior Publication Data
US 2016/0365236 A1    Dec. 15, 2016

(30) Foreign Application Priority Data

Feb. 4, 2014  (EP) .................................... 14153855
Feb. 4, 2014  (GB) .................................... 1401881.6

(51) Int. Cl.
*H01J 49/00* (2006.01)
*H01J 49/42* (2006.01)
*G01N 30/72* (2006.01)

(52) U.S. Cl.
CPC ...... *H01J 49/4215* (2013.01); *G01N 30/7233* (2013.01); *H01J 49/0031* (2013.01); *H01J 49/0036* (2013.01); *G01N 30/72* (2013.01)

(58) Field of Classification Search
CPC ............... H01J 49/4215; H01J 49/0031; H01J 49/0036; G01N 30/7233; G01N 30/72
(Continued)

(56) References Cited

U.S. PATENT DOCUMENTS 8,053,723 B2   11/2011   Senko
8,063,358 B2   11/2011   Bateman et al.
(Continued)

FOREIGN PATENT DOCUMENTS

JP   H10213567      8/1988
JP   2006/189279    7/2006
(Continued)

OTHER PUBLICATIONS

Peter Stone et al., "New Dynamic MRM Mode Improves Data Quality and Triple Quad Quantification in Complex Analyses", Agilent Technologies, Santa Clara, California, Jun. 2009.
(Continued)

*Primary Examiner* — Michael Maskell
(74) *Attorney, Agent, or Firm* — Womble Bond Dickinson (US) LLP; Deborah M. Vernon; Heath T. Misley

(57) ABSTRACT

A method of mass spectrometry is disclosed comprising monitoring for the emergence of one or more species of ions of interest and determining during the course of acquiring experimental data whether one or more ions or interest have emerged and then discontinuing monitoring for the emergence of the one or more species of ions of interest if it determined that the one or more ions or interest have emerged.

18 Claims, 1 Drawing Sheet

(58) Field of Classification Search
USPC .................................... 250/281, 282, 288
See application file for complete search history.

(56) References Cited

U.S. PATENT DOCUMENTS

| | | | | |
|---|---|---|---|---|
| 2007/0090287 A1* | 4/2007 | Foote | ................... | H01J 49/025 |
| | | | | 250/292 |
| 2007/0114374 A1* | 5/2007 | Prest | ................... | H01J 49/025 |
| | | | | 250/282 |
| 2009/0236513 A1 | 9/2009 | Lock et al. | | |
| 2010/0108878 A1 | 5/2010 | Bateman et al. | | |
| 2010/0301201 A1* | 12/2010 | Gordon | ............... | H01J 49/0036 |
| | | | | 250/282 |
| 2015/0247829 A1* | 9/2015 | Sumiyoshi | ......... | G01N 30/8651 |
| | | | | 250/288 |

FOREIGN PATENT DOCUMENTS

| | | |
|---|---|---|
| WO | 2006/054101 | 5/2006 |
| WO | 2008/139193 | 11/2008 |

OTHER PUBLICATIONS

"Agilent Technologies Agilent 6400 Series Triple Quadrupole LC/MS System", Agilent Technologies, Santa Clara, California, Nov. 2012.
R. Kiyonami et al., "Increased Selectivity, Analytical Precision, and Throughput in Targeted Proteomics", Molecular & Cellular Proteomics, vol. 10, No. 2, Feb. 2011.
Vinzenz Lange et al., "Selected reaction monitoring for quantitative proteomics: a tutorial" Molecular Systems Biology, vol. 4, Oct. 2008.

\* cited by examiner

OPTIMIZED MULTIPLE REACTION MONITORING OR SINGLE ION RECORDING METHOD

CROSS REFERENCE TO RELATED APPLICATIONS

This application is the National Stage of International Application No. PCT/GB2015/050300, filed 4 Feb. 2015 which claims priority from and the benefit of United Kingdom patent application No. 1401881.6 filed on 4 Feb. 2014 and European patent application No. 14153855.3 filed on 4 Feb. 2014. The entire contents of these applications are incorporated herein by reference.

BACKGROUND TO THE PRESENT INVENTION

The present invention relates to a method of mass spectrometry and a mass spectrometer.

It is known to use a single quadrupole mass filter or a tandem quadrupole mass filter arrangement to perform targeted quantitative analysis. For example, it is known to perform a Single Ion Recording ("SIR") experiment wherein a single quadrupole mass filter is set so as to only transmit ions having a mass to charge ratio which corresponds to a target analyte of interest within a time window which corresponds to the expected elution time of the target analyte of interest. If multiple target analytes of interest are monitored for at the same time then the resulting signal recorded by an ion detector for a particular target analyte of interest may be summed for a time interval which is significantly shorter than the chromatographic elution time of a single species of analyte of interest. This is called the dwell time. Repetitively monitoring the detector output during several dwell times allows the profile of the eluting chromatographic peak to be recorded. The signal may then be subsequently integrated in order to quantify the targeted analyte of interest.

In a similar manner, a tandem quadrupole arrangement may be used to monitor for a transition from a selected precursor or parent ion of interest which is then fragmented in a collision cell to form product ions. Particular or selected product ions of interest may then be monitored for each analyte. Such an approach is known as Multiple Reaction Monitoring ("MRM").

In conventional MRM or SIR experiments using quadrupole mass filters it is common for several target mass to charge ratios to be simultaneously monitored and several different target analytes may elute within a similar time period.

According to a conventional approach analyte ions are monitored for sequentially and repetitively such that the interval between signal acquired for each analyte is sufficient to profile the chromatographic elution profile.

For a quadrupole mass filter operated with resolving DC only one species of ions having a particular mass to charge ratio can be monitored for at any particular time. Accordingly, sequentially switching between multiple mass to charge ratios will result in a reduction in the duty cycle and hence the ultimate sensitivity of the system will also be reduced.

The time window during which a particular analyte ion is monitored may be based upon the chromatographic retention time determined using pure standards of the target analytes during a precalibration procedure. For many LC-MS analyses this window is often relatively large compared to the width of an individual chromatographic peak as it is known that the retention time can change unpredictably for a variety of reasons.

The more transitions monitored for in a particular window then the lower the resulting duty cycle of any specific transition and hence the lower ultimate detection limit of all analytes in the time window.

The reason for using a relatively large time window is partly to simplify method development but also more fundamentally to ensure that shifts in retention time do not result in missed transitions and false negatives. Chromatographic peak shifts can occur because of column aging or the presence of matrix or contaminant co-eluting species which can affect the chemistry of the column or because of pH changes in the matrix. These effects can even reverse the elution order of target analytes.

Even though the exact retention time of each component within a retention time window is not deterministic it is likely that some of the analytes will be chromatographically resolved within a given time window. This means that within a retention time window some analyte transitions will continue to be monitored even after they have eluted from the column.

Reiko Kiyonami et al. "Increased Selectivity, Analytical Precision, and Throughput in Targeted Proteomics", Molecular & Cellular Proteomics, vol. 10, no. 2, 1 Feb. 2011, ISSN: 1535-9476 discloses a method of selected reaction monitoring wherein a first set of primary transitions are continuously monitored during a predefined elution time window. A set of six to eight transitions is acquired in a data-dependent event, triggered when all of the primary transitions exceed a preset threshold.

US 2007/0114374 (Prest) discloses a method for dynamically adjusting the time period of ion detection. In one arrangement, the dwell time may be dynamically altered during the course of experimental acquisition according to properties of the detected signal (e.g. strength or variability).

US 2009/0236513 (Lock) discloses a method of mass spectrometry wherein a designated "trigger ion" is filtered for, fragmented, and then a designated "trigger ion fragment" is scanned for. Upon detection of the designated trigger ion fragment, at least one "confirmatory ion fragment" is scanned for.

It is desired to provide an improved method of mass spectrometry and an improved mass spectrometer.

SUMMARY OF THE PRESENT INVENTION

According to an aspect of the present invention there is provided a method of mass spectrometry comprising:

monitoring for the emergence of one or more species of ions of interest; and determining during the course of acquiring experimental data whether one or more ions of interest have emerged and then discontinuing monitoring for the emergence of said one or more species of ions of interest if it is determined that said one or more ions or interest have emerged.

Thus the present invention is distinct from the method disclosed in US 2007/0114374 (Prest), wherein the dwell time for a particular ion species of interest may be dynamically altered during the course of experimental acquisition according to properties of the detected signal. In the present invention, by contrast, monitoring for a species of ion may be discontinued altogether upon determination that that species of ion has emerged.

According to a preferred embodiment of the present invention, the step of determining during the course of acquiring experimental data whether or not one or more ions of interest have emerged comprises determining whether or not one or more ions of interest have completed eluting.

According to a preferred embodiment of the present invention, the step of discontinuing monitoring for the emergence of one or more species of ions takes place prior to the expiration of a retention time window associated with said one or more species of ions of interest.

Thus according to a preferred embodiment of the present invention, the monitoring of a particular analyte is preferably stopped once it is determined that that analyte has completed eluting, and before the expiration of a chromatographic retention time window associated with that analyte. As discussed above, the chromatographic retention time window associated with a particular analyte is often relatively large compared to the width of an individual chromatographic peak associated with that analyte (due to the fact that the retention time can vary unpredictably). Thus by determining that an analyte has completed eluting, and then discontinuing the monitoring of a particular species of ion of interest on the basis of this determination but before the expiration of the (relatively vast) retention time window associated with that ion of interest, the method results in an increased duty cycle for any other remaining analytes that are being monitored for.

As will be understood, the approach according to the present invention is distinct from the methods described in Reiko Kiyonami et al. "Increased Selectivity, Analytical Precision, and Throughput in Targeted Proteomics" and US 2009/0236513 (Lock), wherein the monitoring of a particular analyte is only discontinued after a retention time window associated with that analyte (which is much larger than an individual chromatographic peak width) has elapsed. In the preferred embodiment of the present invention, by contrast, the monitoring of a particular analyte is discontinued after determining that that analyte has completed eluting, and prior to the expiration of a retention time window associated with that analyte.

According to a preferred embodiment of the present invention, the step of determining whether or not one or more ions of interest have completed eluting comprises detecting any chromatographic peak associated with said one or more ions of interest.

According to a preferred embodiment of the present invention, the step of determining whether or not one or more ions of interest have completed eluting comprises determining the start and end time of the any chromatographic peak associated with said one or more ions of interest.

According to an aspect of the present invention there is provided a method of mass spectrometry comprising:
monitoring for one or more transitions; and
determining during the course of acquiring experimental data whether one or more of transitions have finished and then discontinuing monitoring for said one or more transitions if it determined that said one or more of transitions have finished.

The preferred embodiment advantageously results in a significant improvement in the duty cycle of targeted quantitative acquisitions.

According to a preferred embodiment of the present invention signals recorded for each analyte within a corresponding retention time window are preferably processed during the acquisition so that if it is determined that an analyte has eluted then monitoring of that particular transition is preferably stopped during the course of the acquisition.

The approach according to the preferred embodiment preferably results in an increase in the duty cycle for the remaining analytes which are preferably monitored for within the remaining time periods. The process according to the preferred embodiment of preferably discontinuing monitoring for a transition once it is determined that the transition has been completed is preferably repeated as it is determined that each analyte has preferably eluted.

In many MRM analysis two or more transitions are monitored for each analyte to confirm and/or quantify the compound. In this case the approach may be extended such that the signal corresponding to elution of the analyte must be detected in both transitions before the monitoring of the analyte is stopped.

The step of monitoring for the emergence of one or more species of ions of interest preferably comprises performing a Single Ion Recording ("SIR") experiment.

The step of performing a Single Ion Recording experiment preferably comprises:
providing a first mass filter; and
setting the first mass filter so as to onwardly transmit parent or precursor ions having mass to charge ratios within a first mass to charge ratio window.

The first mass filter is preferably arranged so as to attenuate parent or precursor ions having mass to charge ratios outside of the first mass to charge ratio window.

The step of performing a Single Ion Recording experiment preferably further comprises monitoring for the emergence of one or more parent or precursor ions having mass to charge ratios within the first mass to charge ratio window which have been onwardly transmitted by the first mass filter.

The method preferably further comprises separating ions according to one or more physico-chemical properties.

The one or more physico-chemical properties preferably comprises chromatographic retention time.

The step of separating ions according to one or more physico-chemical properties preferably comprises separating ions using a liquid chromatography device.

The step of monitoring for the emergence of one or more species of ions of interest preferably comprises monitoring for the elution of one or more parent or precursor ions of interest.

The step of discontinuing monitoring for the emergence of one or more ions of interest preferably occurs substantially immediately once it is determined that the one or more ions of interest have emerged.

The step of discontinuing monitoring for the emergence of one or more ions of interest preferably occurs after a time delay once it is determined that the one or more ions of interest have emerged.

According to another aspect of the present invention there is provided a method of mass spectrometry comprising:
monitoring for one or more transitions; and
determining during the course of acquiring experimental data whether one or more of transitions have finished and then discontinuing monitoring for the one or more transitions if it determined that the one or more of transitions have finished.

The step of determining during the course of acquiring experimental data whether one or more transitions have finished preferably comprises determining whether or not one or more parent or precursor ions of interest have completed eluting.

The step of determining whether one or more transitions have finished preferably comprises detecting any chromatographic peak associated with said one or more transitions.

The step of determining whether or not one or more transitions have finished eluting preferably comprises determining the start and end time of any chromatographic peak associated with said one or more transitions.

The step of determining whether or not one or more transitions have finished eluting comprises determining the start and end time of any chromatographic peak associated with said one or more transitions.

The step of monitoring for one or more transitions preferably comprises performing a Multiple Reaction Monitoring ("MRM") experiment.

The step of performing a Multiple Reaction Monitoring experiment preferably comprises:

providing a first mass filter and a second mass filter;

setting the first mass filter so as to onwardly transmit parent or precursor ions having mass to charge ratios within a first mass to charge ratio window;

reacting or fragmenting the parent or precursor ions having mass to charge ratios within the first mass to charge ratio window so as to form fragment or product ions; and setting a second mass filter so as to onwardly transmit fragment or product ions having mass to charge ratios within a second mass to charge ratio window, The first mass filter is preferably arranged so as to attenuate parent or precursor ions having mass to charge ratios outside of the first mass to charge ratio window.

The second mass filter is preferably arranged so as to attenuate fragment or product ions having mass to charge ratios outside of the second mass to charge ratio window.

The step of discontinuing monitoring for the one or more transitions is preferably performed if it is determined that a single transition has finished.

The step of discontinuing monitoring for the one or more transitions is preferably performed if it is determined that multiple related transitions have finished.

The multiple related transitions preferably comprise a first transition wherein a first species of parent or precursor ion has fragmented or reacted to form a first species of fragment or product ions and a second transition wherein the same first species of parent or precursor ion has fragmented or reacted to form a second different species of fragment or product ions.

The method preferably further comprises separating ions according to one or more physico-chemical properties.

The one or more physico-chemical properties preferably comprises chromatographic retention time.

The step of separating ions according to one or more physico-chemical properties preferably comprises separating ions using a liquid chromatography device.

The step of monitoring for one or more transitions preferably comprises monitoring for the elution of one or more parent or precursor ions of interest which are subsequently reacted or fragmented so as to form one or more product or fragment ions of interest.

The step of preferably discontinuing monitoring for one or more transitions occurs substantially immediately once it is determined that the one or more transitions have finished.

The step of discontinuing monitoring for one or more transitions preferably occurs after a time delay once it is determined that the one or more transitions have finished.

According to another aspect of the present invention there is provided a method of mass spectrometry comprising performing the following steps during a single experimental acquisition:

(i) monitoring for a first transition and one or more second different transitions; and (ii) determining during the course of the experimental acquisition whether or not the first transition has completed wherein if it determined that the first transition has completed then the method further comprises discontinuing monitoring for the first transition and continuing monitoring just for the one or more second transitions.

According to another aspect of the present invention there is provided a method of mass spectrometry comprising performing the following steps during a single experimental acquisition:

(i) monitoring for a first parent ion or a first transition of interest;

(ii) monitoring for a second parent ion or a second transition of interest; and (iii) optionally monitoring for one or more third parent ions or one or more third transitions of interest; and (iv) determining whether the first parent ion has completed eluting or the first transition of interest has completed, wherein if it is determined that the first parent ion has not completed eluting or the first transition of interest has not completed then the method further comprises repeating steps (i)-(iii) and wherein if it is determined that the first parent ion has completed eluting or the first transition of interest has completed then the method further comprises repeating steps (ii) and (iii) without repeating step (i).

According to the preferred embodiment the above steps are performed sequentially and/or repetitively.

According to another aspect of the present invention there is provided a method of mass spectrometry comprising:

monitoring for the emergence of one or more species of ions of interest; and determining during the course of acquiring experimental data whether one or more ions or interest have emerged and then shortening a dwell time of monitoring for the emergence of the one or more species of ions of interest if it determined that the one or more ions or interest have emerged.

Preferably, if it is determined during the course of acquiring experimental data that one or more ions or interest have emerged then a dwell time for monitoring for the emergence of one or more other species of ions is adjusted or lengthened.

According to another aspect of the present invention there is provided a method of mass spectrometry comprising:

monitoring for one or more transitions; and determining during the course of acquiring experimental data whether one or more of transitions have finished and then shortening a dwell time of monitoring for the one or more transitions if it determined that the one or more of transitions have finished.

Preferably, if it is determined during the course of acquiring experimental data that one or more transitions have finished then a dwell time for monitoring for other transitions is adjusted or lengthened.

According to another aspect of the present invention there is provided a mass spectrometer comprising:

a control system arranged and adapted:

(i) to monitor for the emergence of one or more species of ions of interest; and (ii) to determine during the course of acquiring experimental data whether one or more ions or interest have emerged and then to discontinue monitoring for the emergence of the one or more species of ions of interest if it determined that the one or more ions or interest have emerged.

According to another aspect of the present invention there is provided a mass spectrometer comprising:

a control system arranged and adapted to:

(i) to monitor for one or more transitions; and (ii) to determine during the course of acquiring experimental data whether one or more of transitions have finished and then to discontinue monitoring for the one or more transitions if it determined that the one or more of transitions have finished.

According to another aspect of the present invention there is provided a mass spectrometer comprising:

a control system arranged and adapted to:

(i) to monitor for a first transition and one or more second different transitions; and (ii) to determine during the course of an experimental acquisition whether or not the first transition has completed wherein if it determined that the first transition has completed then the control system discontinues monitoring for the first transition and continues monitoring just for the one or more second transitions.

According to another aspect of the present invention there is provided a mass spectrometer comprising:

a control system arranged and adapted to:

(i) to monitor for a first parent ion or a first transition of interest;

(ii) to monitor for a second parent ion or a second transition of interest; and (iii) optionally to monitor for one or more third parent ions or one or more third transitions of interest; and (iv) to determine whether the first parent ion has completed eluting or the first transition of interest has completed, wherein if it is determined that the first parent ion has not completed eluting or the first transition of interest has not completed then the control system is arranged to continue monitoring for the first parent ion or the first transition of interest, the second parent ion or the second transition of interest and optionally the one or more third parent ions or the one or more third transitions of interest; and wherein if it is determined that the first parent ion has completed eluting or the first transition of interest has completed then the control system is arranged to monitor for the second parent ion or the second transition of interest and optionally the one or more third parent ions or the one or more third transitions of interest without monitoring for the first parent ion or the first transition of interest.

According to another aspect of the present invention there is provided a mass spectrometer comprising:

a control system arranged and adapted to:

(i) to monitor for the emergence of one or more species of ions of interest; and (ii) to determine during the course of acquiring experimental data whether one or more ions or interest have emerged and then to shorten a dwell time of monitoring for the emergence of the one or more species of ions of interest if it determined that the one or more ions or interest have emerged.

According to another aspect of the present invention there is provided a mass spectrometer comprising:

a control system arranged and adapted to:

(i) to monitor for one or more transitions; and (ii) to determine during the course of acquiring experimental data whether one or more of transitions have finished and then to shorten a dwell time of monitoring for the one or more transitions if it determined that the one or more of transitions have finished.

According to an aspect of the present invention there is provided a method of mass spectrometry comprising:

monitoring for one or more transitions; and discontinuing monitoring for a first transition if it determined during the course of acquiring data that said first transition has completed.

According to an aspect of the present invention a method of operating an analytical filtering device or combination of analytical filtering devices is provided comprising:

dynamically changing the operational parameters or settings of the filter or filters to allow transmission of a plurality of analyte species during a time period T1;

monitoring the signal at each setting of the analytical filter at a detector downstream during the time period T1; and in response to the detected signal at one or more of the settings of the filter, reducing the number of settings to change during a time period T2, in order to maximise the overall duty cycle of the analytes transmitted.

The analytical filter is preferably either a quadrupole mass filter and/or a differential ion mobility filter.

According to an embodiment the mass spectrometer may further comprise:

(a) an ion source selected from the group consisting of: (i) an Electrospray ionisation ("ESI") ion source; (ii) an Atmospheric Pressure Photo Ionisation ("APPI") ion source; (iii) an Atmospheric Pressure Chemical Ionisation ("APCI") ion source; (iv) a Matrix Assisted Laser Desorption Ionisation ("MALDI") ion source; (v) a Laser Desorption Ionisation ("LDI") ion source; (vi) an Atmospheric Pressure Ionisation ("API") ion source; (vii) a Desorption Ionisation on Silicon ("DIOS") ion source; (viii) an Electron Impact ("EI") ion source; (ix) a Chemical Ionisation ("CI") ion source; (x) a Field Ionisation ("FI") ion source; (xi) a Field Desorption ("FD") ion source; (xii) an Inductively Coupled Plasma ("ICP") ion source; (xiii) a Fast Atom Bombardment ("FAB") ion source; (xiv) a Liquid Secondary Ion Mass Spectrometry ("LSIMS") ion source; (xv) a Desorption Electrospray Ionisation ("DESI") ion source; (xvi) a Nickel-63 radioactive ion source; (xvii) an Atmospheric Pressure Matrix Assisted Laser Desorption Ionisation ion source; (xviii) a Thermospray ion source; (xix) an Atmospheric Sampling Glow Discharge Ionisation ("ASGDI") ion source; (xx) a Glow Discharge ("GD") ion source; (xxi) an Impactor ion source; (xxii) a Direct Analysis in Real Time ("DART") ion source; (xxiii) a Laserspray Ionisation ("LSI") ion source; (xxiv) a Sonicspray Ionisation ("SSI") ion source; (xxv) a Matrix Assisted Inlet Ionisation ("MAII") ion source; (xxvi) a Solvent Assisted Inlet Ionisation ("SAII") ion source; (xxvii) a Desorption Electrospray Ionisation ("DESI") ion source; and (xxviii) a Laser Ablation Electrospray Ionisation ("LAESI") ion source; and/or (b) one or more continuous or pulsed ion sources; and/or (c) one or more ion guides; and/or (d) one or more ion mobility separation devices and/or one or more Field Asymmetric Ion Mobility Spectrometer devices; and/or (e) one or more ion traps or one or more ion trapping regions; and/or (f) one or more collision, fragmentation or reaction cells selected from the group consisting of: (i) a Collisional Induced Dissociation ("CID") fragmentation device; (ii) a Surface Induced Dissociation ("SID") fragmentation device; (iii) an Electron Transfer Dissociation ("ETD") fragmentation device; (iv) an Electron Capture Dissociation ("ECD") fragmentation device; (v) an Electron Collision or Impact Dissociation fragmentation device; (vi) a Photo Induced Dissociation ("PID") fragmentation device; (vii) a Laser Induced Dissociation fragmentation device; (viii) an infrared radiation induced dissociation device; (ix) an ultraviolet radiation induced dissociation device; (x) a nozzle-skimmer interface fragmentation device; (xi) an in-source fragmentation device; (xii) an in-source Collision Induced Dissociation fragmentation device; (xiii) a thermal or temperature source fragmentation device; (xiv) an electric field induced fragmentation device; (xv) a magnetic field induced fragmentation device; (xvi) an enzyme digestion or enzyme degradation fragmentation device; (xvii) an ion-ion reaction fragmentation device; (xviii) an ion-molecule reaction fragmentation device; (xix) an ion-atom reaction fragmentation device; (xx) an ion-metastable ion reaction fragmentation device; (xxi) an ion-metastable molecule reaction fragmentation device; (xxii) an ion-metastable atom reaction fragmentation device; (xxiii) an ion-ion reaction device for reacting ions to form adduct or product ions; (xxiv) an ion-molecule reaction device for reacting ions to form adduct or product ions; (xxv) an ion-atom reaction device for reacting ions to form adduct or product ions; (xxvi) an ion-metastable ion reaction device for reacting ions to form adduct or product ions; (xxvii) an ion-metastable molecule reaction device for reacting ions to form adduct or product ions; (xxviii) an ion-metastable atom reaction device for reacting ions to form adduct or product ions; and (xxix) an Electron Ionisation Dissociation ("EID") fragmentation device; and/or (g) a mass analyser selected from the group consisting of: (i) a quadrupole mass analyser; (ii) a 2D or linear quadrupole mass analyser; (iii) a Paul or 3D quadrupole mass analyser; (iv) a Penning trap mass analyser; (v) an ion trap mass analyser; (vi) a magnetic sector mass analyser; (vii) Ion Cyclotron Resonance ("ICR") mass analyser; (viii) a Fourier Transform Ion Cyclotron Resonance ("FTICR") mass analyser; (ix) an electrostatic mass analyser arranged to generate an electrostatic field having a quadro-logarithmic potential distribution; (x) a Fourier Transform electrostatic mass analyser; (xi) a Fourier Transform mass analyser; (xii) a Time of Flight mass analyser; (xiii) an orthogonal acceleration Time of Flight mass analyser; and (xiv) a linear acceleration Time of Flight mass analyser; and/or (h) one or more energy analysers or electrostatic energy analysers; and/or (i) one or more ion detectors; and/or (j) one or more mass filters selected from the group consisting of: (i) a quadrupole mass filter; (ii) a 2D or linear quadrupole ion trap; (iii) a Paul or 3D quadrupole ion trap; (iv) a Penning ion trap; (v) an ion trap; (vi) a magnetic sector mass filter; (vii) a Time of Flight mass filter; and (viii) a Wien filter; and/or (k) a device or ion gate for pulsing ions; and/or (l) a device for converting a substantially continuous ion beam into a pulsed ion beam.

The mass spectrometer may further comprise either:

(i) a C-trap and a mass analyser comprising an outer barrel-like electrode and a coaxial inner spindle-like electrode that form an electrostatic field with a quadro-logarithmic potential distribution, wherein in a first mode of operation ions are transmitted to the C-trap and are then injected into the mass analyser and wherein in a second mode of operation ions are transmitted to the C-trap and then to a collision cell or Electron Transfer Dissociation device wherein at least some ions are fragmented into fragment ions, and wherein the fragment ions are then transmitted to the C-trap before being injected into the mass analyser; and/or (ii) a stacked ring ion guide comprising a plurality of electrodes each having an aperture through which ions are transmitted in use and wherein the spacing of the electrodes increases along the length of the ion path, and wherein the apertures in the electrodes in an upstream section of the ion guide have a first diameter and wherein the apertures in the electrodes in a downstream section of the ion guide have a second diameter which is smaller than the first diameter, and wherein opposite phases of an AC or RF voltage are applied, in use, to successive electrodes.

According to an embodiment the mass spectrometer further comprises a device arranged and adapted to supply an AC or RF voltage to the electrodes. The AC or RF voltage preferably has an amplitude selected from the group consisting of: (i) <50 V peak to peak; (ii) 50-100 V peak to peak; (iii) 100-150 V peak to peak; (iv) 150-200 V peak to peak; (v) 200-250 V peak to peak; (vi) 250-300 V peak to peak; (vii) 300-350 V peak to peak; (viii) 350-400 V peak to peak; (ix) 400-450 V peak to peak; (x) 450-500 V peak to peak; and (xi) >500 V peak to peak.

The AC or RF voltage preferably has a frequency selected from the group consisting of: (i) <100 kHz; (ii) 100-200 kHz; (iii) 200-300 kHz; (iv) 300-400 kHz; (v) 400-500 kHz; (vi) 0.5-1.0 MHz; (vii) 1.0-1.5 MHz; (viii) 1.5-2.0 MHz; (ix) 2.0-2.5 MHz; (x) 2.5-3.0 MHz; (xi) 3.0-3.5 MHz; (xii) 3.5-4.0 MHz; (xiii) 4.0-4.5 MHz; (xiv) 4.5-5.0 MHz; (xv) 5.0-5.5 MHz; (xvi) 5.5-6.0 MHz; (xvii) 6.0-6.5 MHz; (xviii) 6.5-7.0 MHz; (xix) 7.0-7.5 MHz; (xx) 7.5-8.0 MHz; (xxi) 8.0-8.5 MHz; (xxii) 8.5-9.0 MHz; (xxiii) 9.0-9.5 MHz; (xxiv) 9.5-10.0 MHz; and (xxv) >10.0 MHz.

The mass spectrometer may also comprise a chromatography or other separation device upstream of an ion source. According to an embodiment the chromatography separation device comprises a liquid chromatography or gas chromatography device. According to another embodiment the separation device may comprise: (i) a Capillary Electrophoresis ("CE") separation device; (ii) a Capillary Electrochromatography ("CEC") separation device; (iii) a substantially rigid ceramic-based multilayer microfluidic substrate ("ceramic tile") separation device; or (iv) a supercritical fluid chromatography separation device.

The mass spectrometer may comprise a chromatography detector.

The chromatography detector may comprise a destructive chromatography detector preferably selected from the group consisting of: (i) a Flame Ionization Detector ("FID"); (ii) an aerosol-based detector or Nano Quantity Analyte Detector ("NQAD"); (iii) a Flame Photometric Detector ("FPD"); (iv) an Atomic-Emission Detector ("AED"); (v) a Nitrogen Phosphorus Detector ("NPD"); and (vi) an Evaporative Light Scattering Detector ("ELSD"). Additionally or alternatively, the chromatography detector may comprise a non-destructive chromatography detector preferably selected from the group consisting of: (i) a fixed or variable wavelength UV detector; (ii) a Thermal Conductivity Detector ("TCD"); (iii) a fluorescence detector; (iv) an Electron Capture Detector ("ECD"); (v) a conductivity monitor; (vi) a Photoionization Detector ("PID"); (vii) a Refractive Index Detector ("RID"); (viii) a radio flow detector; and (ix) a chiral detector.

The ion guide is preferably maintained at a pressure selected from the group consisting of: (i) <0.0001 mbar; (ii) 0.0001-0.001 mbar; (iii) 0.001-0.01 mbar; (iv) 0.01-0.1 mbar; (v) 0.1-1 mbar; (vi) 1-10 mbar; (vii) 10-100 mbar; (viii) 100-1000 mbar; and (ix) >1000 mbar. According to an embodiment, analyte ions may be subjected to Electron Transfer Dissociation ("ETD") fragmentation in an Electron Transfer Dissociation fragmentation device. Analyte ions are preferably caused to interact with ETD reagent ions within an ion guide or fragmentation device.

According to an embodiment in order to effect Electron Transfer Dissociation either: (a) analyte ions are fragmented or are induced to dissociate and form product or fragment ions upon interacting with reagent ions; and/or (b) electrons are transferred from one or more reagent anions or negatively charged ions to one or more multiply charged analyte cations or positively charged ions whereupon at least some of the multiply charged analyte cations or positively charged ions are induced to dissociate and form product or fragment ions; and/or (c) analyte ions are fragmented or are induced to dissociate and form product or fragment ions upon interacting with neutral reagent gas molecules or atoms or a non-ionic reagent gas; and/or (d) electrons are transferred from one or more neutral, non-ionic or uncharged basic gases or vapours to one or more multiply charged analyte cations or positively charged ions whereupon at least some of the multiply charged analyte cations or positively charged ions are induced to dissociate and form product or fragment ions; and/or (e) electrons are transferred from one or more neutral, non-ionic or uncharged superbase reagent gases or vapours to one or more multiply charged analyte cations or positively charged ions whereupon at least some of the multiply charge analyte cations or positively charged ions are induced to dissociate and form product or fragment ions; and/or (f) electrons are transferred from one or more neutral, non-ionic or uncharged alkali metal gases or vapours to one or more multiply charged analyte cations or positively charged ions whereupon at least some of the multiply charged analyte cations or positively charged ions are induced to dissociate and form product or fragment ions; and/or (g) electrons are transferred from one or more neutral, non-ionic or uncharged gases, vapours or atoms to one or more multiply charged analyte cations or positively charged ions whereupon at least some of the multiply charged analyte cations or positively charged ions are induced to dissociate and form product or fragment ions, wherein the one or more neutral, non-ionic or uncharged gases, vapours or atoms are selected from the group consisting of: (i) sodium vapour or atoms; (ii) lithium vapour or atoms; (iii) potassium vapour or atoms; (iv) rubidium vapour or atoms; (v) caesium vapour or atoms; (vi) francium vapour or atoms; (vii) $C_{60}$ vapour or atoms; and (viii) magnesium vapour or atoms.

The multiply charged analyte cations or positively charged ions preferably comprise peptides, polypeptides, proteins or biomolecules.

According to an embodiment in order to effect Electron Transfer Dissociation: (a) the reagent anions or negatively charged ions are derived from a polyaromatic hydrocarbon or a substituted polyaromatic hydrocarbon; and/or (b) the reagent anions or negatively charged ions are derived from the group consisting of: (i) anthracene; (ii) 9,10 diphenyl-anthracene; (iii) naphthalene; (iv) fluorine; (v) phenanthrene; (vi) pyrene; (vii) fluoranthene; (viii) chrysene; (ix) triphenylene; (x) perylene; (xi) acridine; (xii) 2,2' dipyridyl; (xiii) 2,2' biquinoline; (xiv) 9-anthracenecarbonitrile; (xv) dibenzothiophene; (xvi) 1,10'-phenanthroline; (xvii) 9' anthracenecarbonitrile; and (xviii) anthraquinone; and/or (c) the reagent ions or negatively charged ions comprise azobenzene anions or azobenzene radical anions.

According to a particularly preferred embodiment the process of Electron Transfer Dissociation fragmentation comprises interacting analyte ions with reagent ions, wherein the reagent ions comprise dicyanobenzene, 4-nitrotoluene or azulene.

BRIEF DESCRIPTION OF THE DRAWINGS

Various embodiments of the present invention will now be described, by way of example only, and with reference to the accompanying drawings in which.

DETAILED DESCRIPTION OF PREFERRED EMBODIMENT

A mass spectrometer according to an embodiment of the present invention will now be described.

According to a preferred embodiment of the present invention a mass spectrometer is provided comprising an ion source which is coupled to a Liquid Chromatography ("LC") separation device. Analytes from a sample will preferably elute from the LC separation device at different times and hence will be ionised by the ion source which preferably comprises an Electrospray ion source at different times. The mass spectrometer preferably further comprises a first quadrupole rod set mass filter Q1 and a collision or fragmentation cell or device which is preferably located downstream of the first quadrupole rod set mass filter Q1. A second quadrupole rod set mass filter Q2 is preferably located downstream of the collision or fragmentation cell or device.

According to an embodiment a Multiple Reaction Monitoring experiment may be performed wherein the first quadrupole rod set mass filter Q1 is arranged to transmit certain specific parent or precursor ions which are then onwardly transmitted to the collision or fragmentation device and are reacted or fragmented so as to form fragment or product ions. The resulting fragment or product ions are then passed to the second quadrupole mass filter Q2 which is preferably arranged to onwardly transmit certain specific fragment or product ions.

Figure 1A:
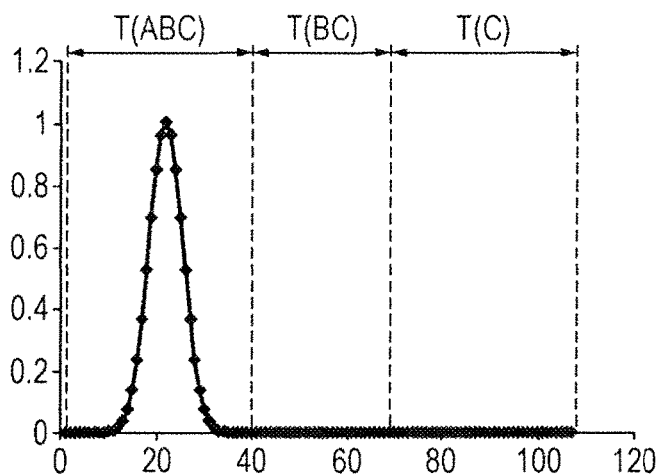
FIG. 1A shows a first chromatographic peak eluting between 0-40 s.
Figure 1B:
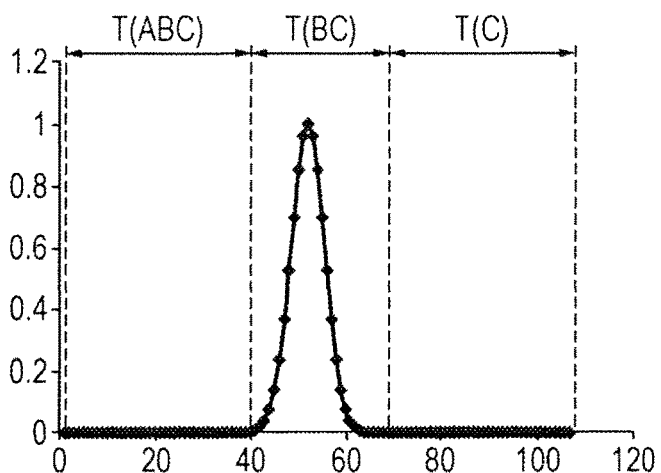
FIG. 1B shows a second chromatographic peak eluting between 40-70 s and FIG. 1C shows a third chromatographic peak eluting between 70-110 s.

FIG. 1A shows a first chromatographic peak which elutes during a first time period T(ABC), FIG. 1B shows a second chromatographic peak which subsequently elutes during a second subsequent time period T(BC) and FIG. 10 shows a third chromatographic peak which subsequently elutes during a yet later time period T(C).

Figure 1C:
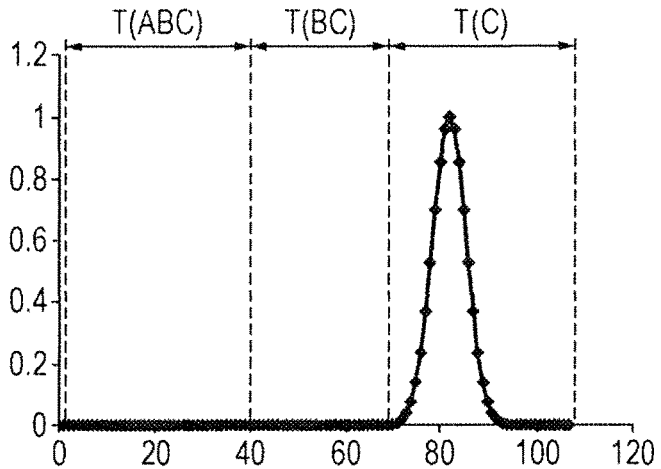

The peaks shown in FIGS. 1A-C represent the signal recorded during an MRM analysis of three analytes using quadrupole mass filters over a total retention time period of T(ABC)+T(BC)+T(C).

FIG. 1A shows the output of the ion detector during dwell times when the first quadrupole Q1 was set to transmit precursor or parent ions having a mass to charge ratio $A_{Pre}$. The precursor or parent ions which were onwardly transmitted by the first quadrupole mass filter Q1 were then arranged to enter a Collision Induced Dissociation ("CID") collision cell whereupon the parent or precursor ions were then fragmented into product ions. The resulting product ions were then passed to the second quadrupole Q2 wherein the second quadrupole Q2 was set to transmit product ions $A_{Prod}$ resulting from CID fragmentation. The fragmentation of parent ions having a mass to charge ratio $A_{Pre}$ and the resulting formation of specific fragment ions having a mass to charge ratio $A_{Prod}$ may be referred to as comprising transition A.

FIG. 1B shows the output of the ion detector during dwell times wherein the first quadrupole Q1 was set to transmit precursor or parent ions having a mass to charge ratio $B_{Pre}$. The precursor or parent ions which were onwardly transmitted by the first quadrupole mass filter Q1 were then arranged to enter the CID collision cell whereupon the parent or precursor ions were fragmented into product ions. The resulting product ions were then passed to the second quadrupole Q2 wherein the second quadrupole Q2 was set to transmit product ion $B_{Prod}$ resulting from CID fragmentation. The fragmentation of parent ions having a mass to charge ratio $B_{Pre}$ and the resulting formation of specific fragment ions having a mass to charge ratio $B_{Prod}$ may be referred to as comprising transition B.

FIG. 1C shows the output of the ion detector during dwell times wherein the first quadrupole Q1 was set to transmit precursor or parent ions having a mass to charge ratio $C_{Pre}$. The precursor or parent ions which were onwardly transmitted by the first quadrupole mass filter Q1 were then arranged to enter the CID collision cell whereupon the parent or precursor ions were fragmented into product ions. The resulting product ions were then passed to the second quadrupole Q2 wherein the second quadrupole Q2 was set to transmit product ions $C_{Prod}$ resulting from CID fragmentation. The fragmentation of parent ions having a mass to charge ratio $C_{Pre}$ and the resulting formation of specific fragment ions having a mass to charge ratio $C_{Prod}$ may be referred to as comprising transition C.

A conventional approach of performing a MRM experiment will now be described.

According to a conventional approach transition A may be monitored for 1 second after which dwell time the first quadrupole Q1 and the second quadrupole Q2 may then be switched to monitor for transition B for 1 second. Thereafter, the first quadrupole Q1 and the second quadrupole Q2 may then be switched again to monitor for transition C for 1 second. After having sequentially monitored for transitions A then B then C, the cycle of acquisition is then repeated so that according to the conventional approach the control system repeatedly monitors for transition A, followed by monitoring for transition B followed by monitoring for transition C. Importantly, this repeated cycling of monitoring for all three transitions continues for the whole duration of a single acquisition of experimental data.

According to the conventional approach the duty cycle for monitoring for each eluting peak or species of ions of interest or each transition is therefore ⅓ (wherein the duty cycle is defined as the total time spent acquiring data for a given transition divided by the total time period over which this particular transition was monitored).

It should be noted that for simplicity an inter channel time between transitions or dwell times has been ignored. An inter channel time between transitions may be provided in order to allow the system to equilibrate at a new set mass or mass to charge ratio. During the inter channel time no experimental data is acquired.

An improved method of performing a MRM experiment according to a preferred embodiment of the present invention will now be described and will be contrasted to the conventional approach as described above.

According to the preferred embodiment and with reference to FIG. 1A during the time period T(ABC) all three transitions are sequentially monitored until it is determined that peak A has eluted. Once it is determined that peak A has completed eluting then from that time onwards the control system preferably switches so that only transitions B and C are preferably monitored for in a sequential manner going forwards.

The process of just monitoring for transitions B and C (and no longer monitoring for transition A) preferably continues throughout subsequent time period T(BC) until it is preferably determined that peak B has completed eluting. Once it is determined that peak B has completed eluting then from that time onwards the control system preferably switches so that only transition C is monitored for over the subsequent time period T(C) and hence transition B is no longer monitored for.

The approach according to the preferred embodiment results in a significant improvement in duty cycle.

According to the preferred embodiment the duty cycle for monitoring for peak A or transition A is 0.33. However, advantageously, the duty cycle for monitoring for peak B or transition B is 0.50 and the duty cycle for monitoring for peak C or transition C is 1 according to the preferred embodiment.

The approach according to the preferred embodiment therefore results in an average duty cycle for the three peaks or three transitions of 0.611. It will be apparent that this represents a significant improvement in the duty cycle compared with the conventional approach wherein the duty cycle was only 0.333. Accordingly, the approach according to the preferred embodiment results in an average duty cycle enhancement of ×1.83.

It will also be apparent that the maximum gain in duty cycle for the last eluting peak (peak C) is a factor of ×3 and the minimum duty cycle (for peak A) is no less than the conventional approach.

The average gain in duty cycle (GaV) may be generalised and is given by the expression:

$$G_{av} = \frac{\sum_{a=0}^{a=(n-1)} \frac{1}{(n-a)}}{n} \quad (1)$$

wherein n is the number of analyte precursor peaks.

Eqn. 1 holds for situations wherein all the peaks within the window are completely resolved and wherein the number of MRM transitions for each precursor ion is the same.

The maximum gain in duty cycle possible for any individual peak Gmax is:

$$G_{max} = n \quad (2)$$

For example, if ten peaks are monitored then Gav=2.93 and Gmax=10.

In practice, chromatographic peaks from several transitions may partially or completely co-elute leading to more complex overall and individual duty cycle gains.

In order to maintain quantitative performance the duty cycle maintained for each peak or each data point in each peak is preferably recorded and may be corrected for in the final reporting of peak area and conversion to analyte concentration from any calibration data.

The approach according to the preferred embodiment is particularly applicable and effective in analysis where not only many transitions may be monitored during extended time periods but also wherein most of the transitions will produce a measurable signal.

In contrast, in pesticide analysis of food products many transitions may be monitored but in many cases no signal or very few signals are recorded. Accordingly, in such scenarios the advantage in sensitivity gain according to the preferred embodiment may be relatively modest as a signal from a transition must be detected before that transition can then cease to be monitored.

However, in many other applications it may be desired to monitor for multiple transitions and most or all of these transitions will actually occur and hence will result in chromatographic peaks being observed.

Accordingly, there are many situations wherein the method according to the preferred embodiment will result in a significant improvement in sensitivity.

One particular application which the preferred embodiment is particularly suited for is targeted proteomics experiments wherein, for example, MRM transitions are determined from a previous screening or MSe analysis and target proteins are then quantified by monitoring characteristic peptide ions and their fragments in a complex MRM experiment using a triple quadrupole mass spectrometer. In such scenarios most of the analyte channels will be likely to contain data and hence the maximum increase in duty cycle according to the preferred embodiment will be realised in practice. Similarly, quantification of metabolites discovered by MSe type analysis will also be improved according to the preferred embodiment.

Various different methods may be employed to determine whether or not a particular target compound has eluted or a transition has completed and hence therefore whether or not the control system can cease monitoring for a particular target compound or can cease monitoring for a particular transition.

According to an embodiment the start and end time of any chromatographic peak associated with a particular analyte monitored can be determined.

The signal for each species preferably consists of intensity information which may be written to disk at each time interval in which that species is being monitored. Various filtering and peak detection techniques may be employed to interrogate the data stream as it is being produced to determine the start and end of a signal, retention time, area and other higher order characteristics of the chromatographic peak. This type of analysis is particularly suited to high speed electronics such as field programmable gate arrays FPGA or other digital signal processing approaches.

A selection of peak recognition and/or peak detection approaches are described below for illustrative purposes only. It will be appreciated that various other methods may be employed.

According to one embodiment an amplitude threshold may be applied directly to the incoming data such that signals having an amplitude falling below a certain value are either set to zero or are set to the threshold value. This approach eliminates some statistical noise which may lead to spurious signals. Alternatively, an adaptive real time background subtraction algorithm such as is disclosed in WO 2008/139193 (which is incorporated herein by reference) may be applied to the data in order to determine the threshold in the presence of background noise.

According to another embodiment the start and end times of an eluting peak may be determined by examining when the signal rises above a threshold and then passes below the threshold. Data within this region may then be further processed in order to determine the centre of mass or centroid and higher order moments in order to aid in peak identification.

According to an embodiment data may first be smoothed by passing the data through a finite impulse response filter such as a moving average or boxcar smoothing filter.

According to another embodiment a method employing a single or double differential may be employed. For example, according to an embodiment a peak detection method such as is disclosed in U.S. Pat. No. 8,063,358 (which is incorporated herein by reference) may be utilised.

Once the start and end of a chromatographic peak have preferably been determined then according to the preferred embodiment the area (first moment) and/or retention time (second moment) and/or higher order moments (skew and kurtosis) may preferably be calculated.

According to an embodiment the detected peak is preferably assessed in order to judge the likelihood that it corresponds to the presence of the targeted analyte before monitoring of the particular analyte is allowed to cease.

Various methods of assessing the data are contemplated and may be utilised according to the preferred embodiment. For example, some signals may be easily discounted based upon comparing the width of the peak determined during detection to the known chromatographic peak width. If the detected peak width is too wide or too narrow within limits then according to the preferred embodiment the analyte should continue to be monitored for. In a similar manner according to another embodiment an area threshold may be applied relative to the integrated area of the detected peak preferably within the start and end times determined. If the signal is very weak then there may be calculable statistical uncertainty associated with the peak. In this case the system may continue to monitor for the analyte.

In many MRM analysis more than one product ion resulting from a single precursor or parent ion may be monitored for. The presence of both product ion peaks preferably with the same retention time and preferably having substantially the same peak shape and optionally wherein the product ions peaks are determined to have a characteristic intensity ratio may be used to determine whether or not the analyte should continue to be monitored for.

According to an embodiment one or more isotopically labelled internal standards may be introduced and may be monitored for with the sample. The presence of a peak corresponding to an internal standard along with the presence of the analyte peak may be used as a check.

In the case where internal standards are introduced for each analyte then there will often be a duty cycle improvement using the method disclosed as these signals will appear in every injection regardless of the presence of analyte.

In addition in some analyses more than one isotope peak of the analyte may be monitored for. For example, analysis for toxins such as dioxin and furan may be performed using a GC-MS high resolution magnetic sector mass spectrometer arranged to operate in a SIR mode of operation. According to an embodiment chlorine isotope ratios appearing in different SIR channels may be monitored. According to the preferred embodiment the retention time and/or chromatographic peak shape and/or ratio of areas may be interrogated as the peak elutes.

According to a further embodiment of the present invention the methods according to the preferred embodiment as described above may be extended by the addition of a mobility separation within each dwell time.

The measurement of drift time or collision cross section ("CCS") and/or IMS peak shape or other ion mobility characteristic may also be utilised in order to compare with that expected of the analyte and this combined with the chromatographic information above to determine if the analyte has indeed eluted.

Once it has been determined that an analyte peak has eluted then according to some embodiments of the present invention it may still be advantageous to continue monitoring that analyte for a certain predetermined time. In particular, this allows baseline data to be collected to assess signal to noise data at a later date.

Various alternative embodiments are also contemplated. According to an embodiment rather than stopping monitoring for a peak once it has been determined that a peak of interest has eluted, the dwell time for the transition may be shorted relative to the dwell time of the other active transitions. This would just be in case a mistake had been made so that there is enough data to indicate that the analysis should be rerun.

The dwell time duration of the remaining transitions may be adjusted to maintain a fixed number of points over each chromatographic peak.

The method according to the preferred embodiment of performing SIR, MRM and MS experiments is particularly suited to be performed using a mass spectrometer such as a quadrupole Time of Flight mass spectrometer, a quadrupole-electrostatic ion trap mass spectrometer such as an ORBITRAP® mass spectrometer. The preferred embodiment may also be implemented using an IMS-QqQ mass spectrometer.

The method according to the preferred embodiment may also be applied to other filters such as FAIMS and/or differential mobility analysers ("DMA").

The method according to the preferred embodiment may be combined with other techniques in order to increase the duty cycle of the experiment. For example, methods wherein the filter is synchronised to the output of an ion mobility spectrometer ("IMS") device or ion trap in a manner as disclosed, for example, in US 2010/0108878 (which is incorporated herein by reference) or wherein multiple precursors or products are allowed through a filter simultaneously as in the case of a quadrupole mass filter with multiple tickle frequency notches such as is disclosed in WO 2006/054101 (incorporated herein by reference) are contemplated.

Although the present invention has been described with reference to preferred embodiments, it will be understood by those skilled in the art that various changes in form and detail may be made without departing from the scope of the invention as set forth in the accompanying claims.

The invention claimed is:

1. A method of mass spectrometry comprising:
during a course of acquiring experimental data, monitoring for the emergence of multiple species of ions of interest; and
determining during the course of acquiring experimental data whether one or more ions of interest have emerged and then discontinuing monitoring for the emergence of said one or more species of ions of interest if it is determined that said one or more ions of interest have emerged, wherein the step of determining during the course of acquiring experimental data whether or not one or more ions of interest have emerged comprises determining whether or not one or more ions of interest have completed eluting; and
continuing to monitor only for the emergence of remaining one or more species ions of interest that have not yet emerged.

2. A method as claimed in claim 1, wherein the step of determining whether or not one or more ions of interest have completed eluting comprises:
detecting any chromatographic peak associated with said one or more ions of interest; or
determining the start and end time of any chromatographic peak associated with said one or more ions of interest.

3. A method as claimed in claim 1, wherein the step of discontinuing monitoring for the emergence of one or more species of ions takes place prior to the expiration of a retention time window associated with said one or more species of ions of interest.

4. A method as claimed in claim 1, wherein the step of monitoring for the emergence of one or more species of ions of interest comprises:
performing a Single Ion Recording ("SIR") experiment; or
monitoring for the elution of one or more parent or precursor ions of interest.

5. A method as claimed in claim 1, further comprising separating ions according to one or more physico-chemical properties.

6. A method as claimed in claim 5, wherein said one or more physico-chemical properties comprises chromatographic retention time.

7. A method as claimed in claim 5, wherein the step of separating ions according to one or more physico-chemical properties comprises separating ions using a liquid chromatography device.

8. A method as claimed in claim 1, wherein the step of discontinuing monitoring for the emergence of one or more ions of interest occurs substantially immediately once it is determined that said one or more ions of interest have emerged or wherein the step of discontinuing monitoring for the emergence of one or more ions of interest occurs after a time delay once it is determined that said one or more ions of interest have emerged.

9. A method of mass spectrometry comprising:
during a course of acquiring experimental data, sequentially and repetitively monitoring for multiple transitions; and
determining during the course of acquiring experimental data whether one or more transitions have finished and then discontinuing monitoring for said one or more transitions if it is determined that said one or more transitions have finished, wherein the step of determining during the course of acquiring experimental data whether one or more transitions have finished comprises determining whether or not one or more parent or precursor ions of interest have completed eluting; and
continuing to sequentially and repetitively monitor only for remaining one or more transitions that have not yet finished, wherein the duty cycle for the remaining one or more transitions that have not yet finished is improved.

10. A method as claimed in claim 9, wherein the step of determining whether one or more transitions have finished eluting comprises:
detecting any chromatographic peak associated with said one or more transitions; or
determining the start and end time of any chromatographic peak associated with said one or more transitions.

11. A method as claimed in claim 9, wherein the step of monitoring for one or more transitions comprises performing a Multiple Reaction Monitoring ("MRM") experiment.

12. A method as claimed in claim 9, wherein said step of discontinuing monitoring for said one or more transitions is performed if it is determined that a single transition has finished or if it is determined that multiple related transitions have finished.

13. A method as claimed in claim 9, wherein the step of monitoring for one or more transitions comprises monitoring for the elution of one or more parent or precursor ions of interest which are subsequently reacted or fragmented so as to form one or more product or fragment ions of interest.

14. A method of mass spectrometry comprising:
monitoring for the emergence of one or more species of ions of interest; and
determining during the course of acquiring experimental data whether one or more ions of interest have emerged and then shortening a dwell time of monitoring for the emergence of said one or more species of ions of interest if it is determined that said one or more ions of interest have emerged, wherein the step of determining during the course of acquiring experimental data whether or not one or more ions of interest have emerged comprises determining whether or not one or more ions of interest have completed eluting.

15. A method as claimed in claim 14, wherein if it is determined during the course of acquiring experimental data that one or more ions of interest have emerged then a dwell time for monitoring for the emergence of one or more other species of ions is adjusted or lengthened.

16. A method of mass spectrometry comprising:
monitoring for one or more transitions; and
determining during the course of acquiring experimental data whether one or more transitions have finished and then shortening a dwell time of monitoring for said one or more transitions if it is determined that said one or more transitions have finished, wherein the step of determining during the course of acquiring experimental data whether one or more transitions have finished comprises determining whether or not one or more parent or precursor ions of interest have completed eluting.

17. A mass spectrometer comprising:
a control system arranged and adapted:
(i) during a course of acquiring experimental data to monitor for the emergence of multiple species of ions of interest; and
(ii) to determine during the course of acquiring experimental data whether one or more ions of interest have emerged and then to discontinue monitoring for the emergence of said one or more species of ions of interest if it is determined that said one or more ions of interest have emerged, wherein the step of determining during the course of acquiring experimental data whether or not one or more ions of interest have emerged comprises determining whether or not one or more ions of interest have completed eluting, and to continue monitoring only for the emergence of remaining one or more species ions of interest that have not yet emerged.

18. A mass spectrometer comprising:
a control system arranged and adapted:
(i) during a course of acquiring experimental data to sequentially and repetitively monitor for multiple transitions; and
(ii) to determine during the course of acquiring experimental data whether one or more transitions have finished and then to discontinue monitoring for said one or more transitions if it determined that said one or more transitions have finished, wherein the step of determining during the course of acquiring experimental data whether one or more transitions have finished comprises determining whether or not one or more parent or precursor ions of interest have completed eluting, and to continue sequentially and repetitively monitoring only for the emergence of remaining one or more transitions that that have not yet finished, wherein the duty cycle for the remaining one or more transitions that have not yet finished is improved.

* * * * *